United States Patent

Maki

[11] Patent Number: 5,808,154
[45] Date of Patent: Sep. 15, 1998

[54] PROCESS FOR THE PRODUCTION OF AN AROMATIC HYDRAZO COMPOUND

[75] Inventor: Hitoshi Maki, Tokyo, Japan

[73] Assignee: Toyo Ink Manufacturing Co., Ltd., Tokyo, Japan

[21] Appl. No.: 924,606

[22] Filed: Jul. 27, 1992

Related U.S. Application Data

[63] Continuation of Ser. No. 668,474, Mar. 13, 1991, abandoned, which is a continuation-in-part of Ser. No. 501,763, Mar. 30, 1990, abandoned.

[30] Foreign Application Priority Data

Apr. 5, 1989  [JP]  Japan ........................................ 1-86362

[51] Int. Cl.$^6$ ........................ C07C 243/00; C09B 27/00
[52] U.S. Cl. ........................ 564/312; 564/311; 534/585
[58] Field of Search ........................ 564/311, 312; 534/585

[56] References Cited

U.S. PATENT DOCUMENTS

| | | | |
|---|---|---|---|
| 2,645,626 | 7/1953 | Sogn | 534/585 |
| 2,684,358 | 7/1954 | Sogn | 534/585 |
| 2,684,359 | 7/1954 | Sogn | 534/585 |
| 2,765,301 | 10/1956 | Cashion | 534/585 |
| 2,804,452 | 8/1957 | Erkkila | 534/585 |
| 3,063,980 | 11/1962 | Bloom et al. | 564/311 |
| 3,156,724 | 11/1964 | Werner et al. | 564/312 |
| 3,821,190 | 6/1974 | Buckwalter | 564/311 |
| 3,931,298 | 1/1976 | Wollensak | 564/402 |
| 4,217,307 | 8/1980 | Planker et al. | 564/311 |
| 4,326,078 | 4/1982 | Herrmann | 564/312 |

FOREIGN PATENT DOCUMENTS

| | | | |
|---|---|---|---|
| 0 000 519 | 2/1979 | European Pat. Off. . | |
| 0 007 972 | 4/1979 | European Pat. Off. . | |
| 0091383 | 10/1983 | European Pat. Off. | 564/311 |
| 0716418 | 10/1954 | United Kingdom | 564/311 |

*Primary Examiner*—Deborah C. Lambkin
*Attorney, Agent, or Firm*—Wenderoth, Lind & Ponack, L.L.P.

[57] ABSTRACT

A process for the production of an aromatic hydrazo compound, which comprises catalytically reducing an aromatic nitro compound with hydrogen in an alkali metal hydroxide aqueous solution and a hydrogen-donating solvent in the presence of a noble metal catalyst and a quinoid compound cocatalyst at a high temperature under a high pressure, the hydrogen-donating solvent being a cyclic hydrocarbon in which hydrogen atoms are attached to its basic skeleton having 1 to 4 aromatic rings and at least one unsaturated carbon-carbon bond remains.

7 Claims, No Drawings

PROCESS FOR THE PRODUCTION OF AN AROMATIC HYDRAZO COMPOUND

This application is a continuation of now abandoned application Ser. No. 668,474, filed Mar. 13, 1991, which application is a continuation-in-part of now abandoned application, Ser. No. 07/501,763 filed Mar. 30, 1990.

FIELD OF THE INVENTION

This invention relates to a process for the production of a hydrazo compound by catalytic reduction of an aromatic nitro compound with hydrogen.

PRIOR ART

An aromatic hydrazo compound is generally produced by a zinc dust process, and it is also produced by a glucose, alcoholate, formalin, alkali hydroxide or iron silicate process. Most of these comprises a two step reaction: the first step comprises converting an aromatic nitro compound to an azoxy or azo compound and then separating this product by a physical procedure, and the second step comprises reducing the separated product into a hydrazo compound. Thus, it must be said that such production processes include complicated steps. Further, these conventional processes mostly include complicated steps for separation and recovery of decomposition products of a reducing agent itself and often produce a waste liquid containing BOD (COD) source substances. Thus, these processes involve difficulties which greatly lower the economy in hydrazo compound production.

U.S. Pat. No. 3,156,724 discloses a one-step process for the production of an aromatic hydrazo compound from an aromatic nitro compound. This process uses a reducing catalyst comprising palladium or platinum. When an aqueous solution containing 2 to 20% by weight of sodium or potassium hydroxide, particularly, an aqueous solution containing 13 to 14% by weight of sodium hydroxide, is used as a reaction medium, the reducing catalyst is used while an organic solvent, particularly a water-immiscible aromatic hydrocarbon, such as benzene, toluene or xylene, is added dropwise. The temperature is 40° to 100° C., particularly 60° to 70° C., and the hydrogen pressure is about 0.4 to 7.8 bar, particularly 0.75 to 1.8 bar. When 2,2'-dichlorohydrazobenzene is produced from o-chloronitrobenzene, a naphthalene derivative, e.g. naphthoquinone-(1,4) or 2,3-dichloro-naphthoquinone-(1,4) is added to a reaction mixture. It is described that the yield of 2,2'-dichlorohydrazobenzene obtained in this procedure varies between 80 and 85% and that chlorine elimination scarcely occurs.

However, the above process not only exhibits a decrease in the yield when a noble metal catalyst is reused from batch to batch, but also requires a longer period of time for the reaction with decreasing activity of the noble metal catalyst. Japanese Laid-Open Patent Publication No. 24838/1979 (U.S. Pat. No. 4,217,307) describes that the catalyst used in one batch shows a decrease in activity when a naphthoquinone compound is used as a cocatalyst. These two results are undesirable to carry out the reduction economically. The chlorine elimination amount of 8% mentioned therein is too high for a first time use.

U.S. Pat. No. 4,326,078 describes a process for the production of an aromatic hydrazo compound from an aromatic nitro compound, which uses an alicyclic hydrocarbon such as cyclohexane as a solvent, a noble metal catalyst and a quinoid compound as a cocatalyst. However, even if such a solvent is used, the activity of the noble metal catalyst decreases. The noble metal catalyst which has been used a few times cannot be used for any further reaction without regenerating it.

Further, U.S. Pat. No. 4,217,307 describes the following. The catalyst can be used for at least ten batches without a decrease in activity and the yield is 83 to 84% at a lower temperature when o-chloronitrobenzene is catalytically reduced into 2,2'-dichlorohydrazobenzene with hydrogen in a sodium hydroxide aqueous solution or a potassium hydroxide aqueous solution, particularly 10 to 25 wt.% sodium hydroxide aqueous solution in the presence of a water-immiscible aromatic solvent, particularly a hydrocarbon such as benzene, toluene or xylene, by using a noble metal catalyst, particularly, palladium, platinum, or modified or sulfidation one (according to U.S. Pat. No. 3,761,425), particularly a sulfidation platinum carbon support catalyst (according to German Patent 2,105,780) under a hydrogen pressure of 1 to about 10 bar, particularly 6 bar and at a reduction temperature of about 50° to 80° C., particularly at 60° C., and, by using, as a cocatalyst, an anthraquinone derivative, particularly a hydroxyanthraquinone such as β-hydroxyanthraquinone or 2,6-dihydroxyanthraquinone.

The process described in U.S. Pat. No. 4,217,307 contributes not to the yield but to a decrease in the chlorine elimination ratio. That is, it is reported that the chlorine elimination ratio is not more than 4% with palladium, not more than 2% with a nonmodified platinum and not more than 1% with sulfidation platinum. However, this process does not satisfactorily decrease the chlorine elimination ratio, nor does it give a satisfactory yield.

SUMMARY OF THE INVENTION

It is an object of this invention to provide a process for the production of an aromatic hydrazo compound, which is economical as compared with any conventional process for the production of an aromatic hydrazo compound.

It is another object of this invention to provide a process for the production of an aromatic hydrazo compound, which can achieve high purity and high yield of the aromatic hydrazo compound as compared with any conventional process.

It is further another object of this invention to provide a process for the production of an aromatic hydrazo compound, which can reduce the amount of an aniline derivative as a by-product.

It is yet another object of this invention to provide a process for the production of an aromatic hydrazo compound, which permits a repeated use of a noble metal catalyst without purifying it or a decrease in activity.

It is still another object of this invention to provide a process for the production of an aromatic hydrazo compound, in which the chlorine elimination amount is small even when a chlorine-substituted aromatic nitro compound is used as a raw material.

It is further another object of this invention to provide a process for the production of an aromatic hydrazo compound, in which the amount of hydrogen required for catalytic reduction is reduced.

According to this invention, there is provided a process for the production of an aromatic hydrazo compound, which comprises catalytically reducing an aromatic nitro compound with hydrogen in an alkali metal hydroxide aqueous solution and a hydrogen-donating solvent in the presence of a noble metal catalyst and a quinoid compound cocatalyst at a high temperature under a high pressure, the hydrogen-donating solvent being a cyclic hydrocarbon in which hydrogen atoms are attached to its basic skeleton having 1 to 4 aromatic rings and at least one unsaturated carbon-carbon bond remains.

DETAILED DESCRIPTION OF THE INVENTION

The aromatic nitro compound of this invention means compounds having 1 to about 3 aromatic rings, such as nitrobenzene, nitronaphthalene, nitroanthracene, etc. And, 1 to 3 halogen groups, carbonyl groups, nitro groups, amino groups, hydroxyl groups, alkyl groups having 1 to 10 carbon atoms or alkenyl groups having 1 to 10 carbon atoms may be optionally substituted in substitutable positions of the rings.

The alkali metal aqueous solution used in this invention means an aqueous solution of sodium hydroxide or potassium hydroxide, and it particularly means an aqueous solution containing 10 to 25% by weight of sodium hydroxide.

The noble metal catalyst means a catalyst prepared by allowing an activated carbon to support palladium or platinum in the presence of hydrogen, and the activated carbon/noble metal weight ratio is 1/0.05.

The hydrogen-donating solvent in this invention means a cyclic hydrocarbon in which hydrogen atoms are attached to its basic skeleton having 1 to 4 aromatic rings and at least one unsaturated carbon-carbon bond remains. Thus, the solvent is a partially hydrogenated aromatic hydrocarbon having 1 to 4 rings. Specifically, it means a cyclic hydrocarbon having a basic skeleton of benzene, naphthalene, anthracene, triphenylene, pyrene, chrysene or naphthacene and having 2 to 18 hydrogen atoms attached. More specifically, its examples are 1,3-cyclohexadiene, 1,4-cyclohexadiene, cyclohexene, 1,2-dihydronaphthalene, 1,4-dihydronaphthalene, tetralin (1,2,3,4-tetrahydronaphthalene), 1,2,3,4,5,6-hexahydronaphthalene, 1,2,3,4,5,8-hexahydronaphthalene, 1,2-dihydroanthracene, 1,4-dihydroanthracene, 2,3-dihydroanthracene, 9,10-dihydroanthracene, 1,2,3,4-tetrahydroanthracene, 1,2,7,8-tetrahydroanthracene, 1,2,9,10-tetrahydroanthracene, 2,3,9,10-tetrahydroanthracene, 2,3,8,9-tetrahydroanthracene, 1,2,3,4,5,6-hexahydroanthracene, 1,2,3,4,5,8-hexahydroanthracene, 1,2,3,4,9,10-hexahydroanthracene, 1,4,5,8,9,10-hexahydroanthracene, 1,2,7,8,9,10-hexahydroanthracene, 2,3,6,7,9,10-hexahydroanthracene, 1,2,3,4,5,6,7,8-octahydroanthracene, 1,2-dihydrophenanthrene, 2,3-dihydrophenanthrene, 1,4-dihydrophenanthrene, 9,10-dihydrophenanthrene, 1,2,3,4-tetrahydrophenanthrene, 1,2,5,6-tetrahydrophenanthrene, 1,2,7,8-tetrahydrophenanthrene, 1,2,9,10-tetrahydrophenanthrene, 2,3,6,7-tetrahydrophenanthrene, 3,4,9,10-tetrahydrophenanthrene, 3,4,5,6-tetrahydrophenanthrene, 1,2,3,4,5,6-hexahydrophenanthrene, 1,2,3,4,9,10-hexahydrophenanthrene, 1,4,5,8,9,10-hexahydrophenanthrene, 1,2,7,8,9,10-hexahydrophenanthrene, 2,3,6,7,9,10-hexahydrophenanthrene, 1,2,3,4,5,6,7,8-octahydrophenanthrene, tetradecahydrophenanthrene, 1,2-dihydrotriphenylene, 2,3-dihydrotriphenylene, 1,4-dihydrotriphenylene, 1,2,3,4-tetrahydrotriphenylene, 1,2,5,6-tetrahydrotriphenylene, 1,2,9,10-tetrahydrotriphenylene, 1,2,3,4,5,6-hexahydrotriphenylene, 1,4,5,8,9,12-hexahydrotriphenylene, 2,3,6,7,10,11-hexahydrotriphenylene, 1,2,3,4,5,6,7,8-octahydrotriphenylene, 1,2-dihydropyrene, 1,2,4,5-tetrahydropyrene, 1,2,6,7-tetrahydropyrene, 1,2,7,8-tetrahydropyrene, 1,2,9,10-tetrahydropyrene, 2,3,4,5-tetrahydropyrene, 1,2-dihydrochrysene, 1,2,3,4-tetrahydrochrysene, 1,2,5,6-tetrahydrochrysene, 1,2,8,9-tetrahydrochrysene, 1,2,11,12-tetrahydrochrysene, 1,2,3,4,7,8,9,10-decahydrochrysene, 1,2-dihydronaphthacene, 5,12-dihydronaphthacene, 1,2,3,4-tetrahydronaphthacene, 1,2,7,8-tetrahydronaphthacene, 2,3,8,9-tetrahydronaphthacene, 1,4,7,10-tetrahydronaphthacene, 5,6,11,12-tetrahydronaphthacene, 1,2,3,4,5,6,11,12-octahydronaphthacene, etc.

The quinoid compound, which is used as a cocatalyst in this invention, means a compound formed of 1 to 3 aromatic rings as a basic skeleton and having no substituent or having one chlorine atom or hydroxyl group substituted in its substitutable position or having two chlorine atoms or two hydroxyl groups substituted in two α-positions, two β-positions or two γ-positions. Its specific examples are o-benzoquinone, 3-chloro-1,2-benzoquinone, 3,-hydroxy-1,2-benzoquinone, 4-chloro-1,2-benzoquinone, 4-hydroxy-1,2-benzoquinone, 3,6-dichloro-1,2-benzoquinone, 3,6-dihydroxy-1,2-benzoquinone, 2,4-dichloro-1,2-benzoquinone, 2,4-dihydroxy-1,2-benzoquinone, p-benzoquinone, 2,5-dichloro-1,4-benzoquinone, 2,5-dihydroxy-1,4-benzoquinone, 2,6-dichloro-1,4-benzoquinone, 2,6-dihydroxy-1,4-benzoquinone, 1,2-naphthoquinone, α-chloro-1,2-naphthoquinone, α-hydroxy-1,2-naphthoquinone, β-chloro-1,2-naphthoquinone, β-hydroxy-1,2-naphthoquinone, 4,5-dichloro-1,2-naphthoquinone, 4,5-dihydroxy-1,2-naphthoquinone, 6,7-dichloro-1,2-naphthoquinone, 6,7-dihydroxy-1,2-naphthoquinone, 1,4-naphthoquinone, α-chloro-1,4-naphthoquinone, α-hydroxy-1,4-naphthoquinone, β-chloro-1,4-naphthoquinone, β-hydroxy-1,4-naphthoquinone, 2,3-dichloro-1,4-naphthoquinone, 2,3-dihydroxy-1,4-naphthoquinone, 5,8-dichloro-1,4-naphthoquinone, 5,8-dihydroxy-1,4-naphthoquinone, 2,6-naphthoquinone, α-chloro-2,6-naphthoquinone, α-hydroxy-2,6-naphthoquinone, β-chloro-2,6-naphthoquinone, β-hydroxy-2,6-naphthoquinone, 1,4-dichloro-2,6-naphthoquinone, 1,4-dihydroxy-2,6-naphthoquinone, 3,7-dichloro-2,6-naphthoquinone, 3,7-dihydroxy-2,6-naphthoquinone, 9,10-anthraquinone, α-chloro-9,10-anthraquinone, α-hydroxy-9,10-anthraquinone, β-chloro-9,10-anthraquinone, β-hydroxy-9,10-anthraquinone, 2,3-dichloro-9,10-anthraquinone, 2,3-dihydroxy-9,10-anthraquinone, 2,6-dichloro-9,10-anthraquinone, 2,6-dihydroxy-9,10-anthraquinone, 1,4-dichloro-9,10-anthraquinone, 1,4-dihydroxy-9,10-anthraquinone, 1,5-dichloro-9,10-anthraquinone, 1,5-dihydroxy-9,10-anthraquinone, 1,2-anthraquinone, α-chloro-1,2-anthraquinone, α-hydroxy-1,2-anthraquinone, β-chloro-1,2-anthraquinone, α-hydroxy-1,2-anthraquinone, 3,7-dichloro-1,2-anthraquinone, 3,7-dihydroxy-1,2-anthraquinone, 3,6-dichloro-1,2-anthraquinone, 3,6-dihydroxy-1,2-anthraquinone, 4,5-dichloro-1,2-anthraquinone, 4,5-dihydroxy-1,2-anthraquinone, 4,8-dichloro-1,2-anthraquinone, 4,8-dihydroxy-1,2-anthraquinone, 1,4-anthraquinone, α-chloro-1,4-anthraquinone, α-hydroxy-1,4-anthraquinone, β-chloro-1,4-anthraquinone, β-hydroxy-1,4-anthraquinone, γ-chloro-1,4-anthraquinone, γ-hydroxy-1,4-anthraquinone, 5,8-dichloro-1,4-anthraquinone, 5,8-dihydroxy-1,4-anthraquinone, 2,3-dichloro-1,4-anthraquinone, 2,3-dihydroxy-1,4-anthraquinone, 2,6-dichloro-1,4-anthraquinone, 2,6-dihydroxy-1,4-anthraquinone, 6,7-dichloro-1,4-anthraquinone, 6,7-dihydroxy-1,4- anthraquinone, 9,10-dichloro-1,4-anthraquinone, 9,10-dihydroxy-1,4-anthraquinone, etc.

The hydrogen-donating solvent in this invention is unstable to a great extent since part of the bonds of its aromatic ring(s) are saturated. Even with a small energy, the hydrogen-donating solvent is oxidized into a stable aromatic compound by releasing hydrogen. When hydrogen is continuously fed to the reaction system, the aromatic compound is reduced again and part of its carbon-carbon unsaturated bonds are saturated. It is assumed that the activity of the noble metal catalyst in this invention is kept stable due to the above activity of the hydrogen-donating solvent.

The process for the production of an aromatic hydrazo compound of this invention will be explained hereinbelow.

An autoclave is charged with an aromatic nitro compound, a hydrogen-donating solvent, an alkali metal hydroxide, a noble metal catalyst, a cocalalyst and, preferably, an emulsifier. The weight ratios of these components are as follows. The hydrogen-donating solvent/aromatic nitro compound=1/0.8 to 1/6.3; alkali metal hydroxide/aromatic nitro compound=1/5 to 1/25; noble metal catalyst/aromatic nitro compound=1/42,000 to 1/1,500; cocatalyst/aromatic nitro compound=1/100 to 1/300; and emulsifier/aromatic nitro compound=1/100 to 1/600. Nitrogen is substituted in the autoclave for air, and further, hydrogen is substituted in the autoclave until the hydrogen initial pressure becomes 3 to 10 kg/cm$^2$. The mixture is heated to 50° to 120° C. while it is stirred. During the reaction, hydrogen is always supplied into the autoclave from the outside of the reaction system such that the pressure inside the autoclave is the same as the pressure shown immediately after the reaction initiation. When the reaction finishes, the pressure inside the autoclave and the reaction temperature are increased by 10 to 25 percent of those shown at the reaction initiation time. After the reduction, the catalyst is separated by filtration while taking care not to bring it into contact with air, and the separated catalyst is recycled into a next batch without purifying it. An aqueous phase is separated from the reaction solution containing a formed aromatic hydrazo compound and an aniline derivative, then the aniline derivative is removed by washing with diluted hydrochloric acid, the solvent is distilled off, and the aromatic hydrazo compound is dried to measure its yield. Since the formed product has a sufficient purity, it is used for direct conversion into benzidines with a mineral acid. The alkali metal is used in a form of an aqueous solution containing preferably 10 to 25% by weight of sodium hydroxide or potassium hydroxide.

The emulsifier used in this invention means an anionic or nonionic surfactant, such as an anionic surfactant containing as a main component a fatty acid salt, alkyl sulfate, alkylbenzene sulfonate, alkylnaphthalene sulfonate, dialkyl succinate, alkyl phosphate, formalin naphthalene sulfonate condensate or polyoxyethylene alkyl sulfate, or a nonionic surfactant containing as a main component polyoxyethylene alkyl ether, polyoxyethylene alkyl phenol ether, polyoxyethylene fatty acid ester, sorbitan fatty acid ester, polyoxyethylene sorbitan fatty acid ester or glycerine fatty acid ester.

This invention uses, as a solvent, a hydrogen-donating compound by which the hydrogen transfer can be expected, whereby there is provided a process for the production of a high-purity aromatic hydrazo compound from an aromatic nitro compound at high yields even if a small amount of a catalyst is used.

When a conventional process uses a naphthoquinone-type compound as a cocatalyst, the noble metal catalyst can be hardly used repeatedly, since its activity is degraded when it is used only once. According to this invention, there is provided a process for the production of an aromatic hydrazo compound, in which the noble metal catalyst does not lose its activity and can therefore be used repeatedly even if the naphthoquinone-type compound is used as a cocatalyst. Further, according to this invention, there is provided a process for the production of an aromatic hydrazo compound at a high yield, in which the noble metal catalyst exhibits high activity and is free from a change in reaction time even if the naphthoquinone-type compound is used in the same amount as that of an anthraquinone compound.

The conventional catalytic reduction of o-chloronitrobenzene into 2,2'-dichlorohydrazobenzene has had a problem that chlorine atoms are eliminated during the reaction. According to this invention, there is provided a process for the production of an aromatic hydrazo compound, in which the amount of eliminated chlorine atoms is not more than 1% by weight of the theoretical value when a palladium catalyst, nonmodified platinum catalyst or the like is used.

According to this invention, there is provided a process for the production of an aromatic hydrazo compound, which is economical since the amount of hydrogen in use is small. This point will be explained below by referring to the use of tetralin as a hydrogen-donating solvent.

During the catalytic reduction, at first, the main reaction uses hydrogen of the hydrogen-donating solvent, tetralin, as well, since it consumes a large amount of hydrogen. Thus, a large part of the tetralin releases hydrogen and changes into naphthalene. And, as the reaction proceeds, the hydrogen consumption amount decreases, and the amount of hydrogen introduced into the reaction system becomes excessive. Hence, the solvent in the form of naphthalene is reduced with hydrogen and changes back to tetralin. Further, due to the presence of a reducing catalyst in the reaction system, part of the tetralin has been further reduced into decalin. Since, however, the amount of the catalyst in the reaction system is not sufficient to reduce all the amount of the tetralin, the reduction comes to an end when part of the tetralin becomes decalin, and the hydrogen consumption also stops. This point of time is an end to the main reaction, and when a product is removed and the solvent is recovered, the solvent is a mixture of tetralin with decalin. When this mixture is used as a solvent for a next catalytic reduction reaction, i.e. a second catalytic reduction reaction or that after the second, the hydrogen consumption amount in this catalytic reduction reaction is only about the theoretical amount in the main reaction. If, however, the hydrogen-donating solvent disclosed in this invention is not used, the hydrogen consumption amount in a second catalytic reduction reaction or that after the second is 1.5 times as large as the theoretical amount.

That is, according to this invention, there is provided a process for the production of an aromatic hydrazo compound, in which the hydrogen consumption amount is small and the yield is high.

According to this invention, there is further provided a process for the production of an aromatic hydrazo compound, in which the amount of aniline derivatives as a by-product is reduced.

According to this invention, the noble metal catalyst can be repeatedly used without purifying it.

EXAMPLES

This invention will be explained hereinbelow according to Examples, in which "part" stands for "part by weight" and "%" for "% by weight".

EXAMPLE 1

A 1-liter autoclave having an electromagnetic stirrer, a heating device and a condenser was charged with the following materials.

o-Chloronitrobenzene 315 g (2 moles)

Tetralin 100 ml

25% Sodium hydroxide aqueous solution 90 g 2,3-Dichloro-1,4-naphthoquinone 2.5 g Emulsifier (a commercially available emulsifier mixture containing sodium dodecylbenzene sulfonate as a main component and small amounts of oleic acid, sodium $C_{13}$–$C_{16}$ alkylsulfamidocarboxylate and a slightly chlorinated long-chain hydrocarbon) 1.7 g 5% Platinum-carbon support catalyst 0.6 g Air within the closed autoclave closed was fully removed with nitrogen, and then, hydrogen was charged under pressure into the autoclave, with fully removing the nitrogen, until the hydrogen pressure became 3 kg/cm$^2$. Hydrogen was always introduced to maintain this pressure. Around the time when the reaction finished, the hydrogen pressure was increased up to 6 kg/cm$^2$. The reaction temperature was increased, by heating, up to 60° C. immediately after the reaction initiation, and when the hydrogen absorption amount decreased, the temperature was increased up to 80° C. The termination of hydrogen absorption was regarded as an end of the reaction. The reduction time was 5 hours. After the reaction, the platinum-carbon support catalyst was thermally filtered from the reaction mixture at 80° C. The filtrate was cooled, and then separated into an organic phase and an aqueous phase. The organic phase (containing 2,2'-dichlorohydrazobenzene and a by-product o-chloroaniline) was washed twice with 5% hydrochloric acid according to a customary manner to elute o-chloroaniline, and the solvent and a precipitate were separated by filtration. The precipitate was fully washed with methanol and dried. Then, the yield was measured: The yield of 2,2'-dichlorohydrazobenzene having a melting point of 85° to 86° C. was 91.5% of the theoretical value and that of o-chloroaniline was 7.5% (both on the basis of o-chloronitrobenzene).

When the 5% platinum-carbon support catalyst was used five times, the yields and the reaction times did not vary. The chlorine elimination amount was 0.8%, at most, of the theoretical value on the basis of o-chloronitrobenzene.

COMPARATIVE EXAMPLE 1

Example 1 was repeated except that 100 ml of "solvent naphtha" was used in place of the tetralin. The reduction time was 7 hours. The yield was 84.0% of the theoretical value on the basis of o-chloronitrobenzene, and that of a by-product ochloroaniline was 10.8%. The chlorine elimination amount was 4.0%, at most, on the basis of o-chloronitrobenzene.

When the platinum-carbon support catalyst was repeatedly used, there was a sharp decrease in yield. For example, when it was used for the second time, the reduction time was 12 hours, and the yield was 47.2% of the theoretical value. The chlorine elimination amount was 5.0%.

EXAMPLE 2

Example 1 was repeated except that 0.6 g of a 5% palladium-carbon support catalyst was used in place of the 5% platinum-carbon support catalyst. The reduction time was 5 hours.

The yield of 2,2'-dichlorohydrazobenzene having a melting point of 85° to 86° C. was 88.9% of the theoretical value on the basis on o-chloronitrobenzene, and that of a by-product o-chloroaniline was 9.7%. The chlorine elimination amount was 0.4%, at most, of the theoretical value on the basis of o-chloronitrobenzene.

COMPARATIVE EXAMPLE 3

Example 1 was repeated except that 100 ml of "solvent naphtha" was used in place of the tetralin. The reduction tint was 8 hours. The yield was 79.5% of the theoretical value on the basis on o-chloronitrobenzene, and that of a by-product ochloroaniline was 13.1%. The chlorine elimination amount was 6.0%, at most, of the theoretical value on the basis of o-chloronitrobenzene.

EXAMPLE 3

Example 1 was repeated except that 2.5 g of 2,6-dihydroxylanthraquinone was used in place of 2,3-dichloro-1,4-naphthoquinone. The reduction time was 7 hours.

The yield of 2,2'-dichlorohydrazobenzene having a melting point of 85° to 86° C. was 84.9% of the theoretical value on the basis on o-chloronitrobenzene, and that of a by-product o-chloroaniline was 12.7%. The chlorine elimination amount was 0.4%, at most, of the theoretical value on the basis of o-chloronitrobenzene. When the 5% platinum-carbon support catalyst was used five times, there was no change in yield and reaction time.

EXAMPLE 4

Example 1 was repeated except that 2,3-dichloro-1,4-naphthoquinone was not used. The reduction time was 8 hours.

The yield of 2,2'-dichlorohydrazobenzene having a melting point of 85° to 86° C. was 83.9% of the theoretical value on the basis on o-chloronitrobenzene, and that of a by-product -ochloroaniline was 9.3%. The chlorine elimination amount was 0.4%, at most, of the theoretical value on the basis of o-chloronitrobenzene. When the 5% platinum-carbon support catalyst was used five times, there was no change in yield and reaction time.

EXAMPLE 5

Example 1 was repeated except that 100 ml of tetrahydronaphthacene in a molten state was used in place of the tetralin. The reduction time was 12 hours.

The yield of 2,2'-dichlorohydrazobenzene having a melting point of 85° to 86° C. was 84.5% of the theoretical value on the basis on o-chloronitrobenzene, and that of a by-product o-chloroaniline was 9.4%. The chlorine elimination amount was 0.2%, at most, of the theoretical value on the basis of o-chloronitrobenzene.

What is claimed is:

1. A process for the production of 2,2'-dichlorohydrazobenzene, which comprises catalytically reducing o-chloronitrobenzene with hydrogen in a sodium hydroxide or potassium hydroxide aqueous solution and tetralin in the presence of a platinum-carbon support catalyst or a palladium-carbon support catalyst and a quinoid compound cocatalyst having a basic skeleton formed of 1 to 3 aromatic rings at a high temperature under a high pressure.

2. A process according to claim 1, wherein the platinum-carbon support catalyst or the palladium-carbon support catalyst has an activated carbon/platinum-carbon support catalyst or palladium-carbon support catalyst weight ratio of 1:0.05.

3. A process according to claim 1, wherein the platinum-carbon support catalyst or the palladium-carbon support catalyst is added in an o-chloronitrobenzene/platinum-carbon support catalyst or palladium-carbon support catalyst weight ratio of from 42,000/1 to 1,500/1.

4. A process according to claim 1, wherein the quinoid compound has one or two substituents of chlorine atoms or hydroxyl groups.

5. A process according to claim 1, wherein the tetralin is used in an o-chloronitrobenzene tetralin weight ratio of from 0.8/1 to 6.3/1.

6. A process according to claim 1, wherein the sodium hydroxide or the potassium hydroxide is used in an o-chloronitrobenzene/sodium hydroxide or potassium hydroxide weight ratio of from 5/1 to 25/1.

7. A process according to claim 1, wherein the quinoid compound is used in an o-chloronitrobenzene/quinoid compound weight ratio of from 100/1 to 300/1.

* * * * *